United States Patent [19]

Procházka et al.

[11] Patent Number: 5,486,596
[45] Date of Patent: Jan. 23, 1996

[54] ANALOGUES OF 8-D-HOMOARGININE VASOPRESSIN

[75] Inventors: Zdenko Procházka; Ivo Bláha; Miroslava Žertová; Jiřina Slaninová; JiříVelek; Jana Škopková; Michal Lebl, all of Prague; Tomislav Barth, Roztoky u Prahy; Lenka Maletínská, Prague, all of Czechoslovakia; Hans Vilhardt, Espergarde, Denmark

[73] Assignee: Ceskoslovenska akademie ved, Czechoslovakia

[21] Appl. No.: 111,815

[22] Filed: Aug. 25, 1993

Related U.S. Application Data

[63] Continuation of Ser. No. 873,967, Apr. 24, 1992, abandoned, which is a continuation-in-part of Ser. No. 564,538, Aug. 7, 1990, abandoned.

[30] Foreign Application Priority Data

Aug. 7, 1989 [CS] Czechoslovakia ...................... 4705-89
Aug. 18, 1989 [CS] Czechoslovakia ...................... 4860-89

[51] Int. Cl.$^6$ ............................ A61K 38/00; C07K 7/06; C07K 7/00
[52] U.S. Cl. ............................ 530/329; 530/315; 514/16
[58] Field of Search .................................. 530/328, 315; 514/16

[56] References Cited

U.S. PATENT DOCUMENTS

| | | | |
|---|---|---|---|
| 4,551,445 | 11/1985 | Manning et al. | 530/315 |
| 4,604,378 | 8/1986 | Callahan et al. | 514/11 |
| 4,749,782 | 6/1988 | Huffman et al. | 530/315 |
| 4,876,243 | 10/1989 | Marshall et al. | 530/315 |

OTHER PUBLICATIONS

Bodanszky et al, "Synthesis and Some Pharmacological Properties of 8–L–Homoarginine–vasopressin and of 1–Deamino–8–L–homoarginine vasopressin", *J. of Med. Chem.*, 17, 781–783, 1974.
Zoral, et al, "Amino Acids and Peptides, LXXI, "Synthesis of 1–Deamino–8–D–γ Aminobutyrine–vasopressin, and 1–Deamino–8–D–Arginine–vasopressin, Collection Czechoslov, Chem. Commun., vol. 32 (1967), 1250–1257.
Zoral, et al., Amino Acids and Peptides. XCVII, Collection Czechoslov. Chem. Commun., vol. 35:1716–1726 (1970).
M. Zaoral et al., "Amino Acids and Peptides. LX. Synthesis of D–DAB$^8$–Vasopressin," *Collection of Czechoslov. Chem. Commun.*, vol. 31:310–314 (1966).
M. Zaoral et al., "Amino Acids and Peptides. LIX. Synthesis and Some Biological Properties of L–DAB$^8$–Vasopressin," *Collection Czechoslov. Chem. Commun.*, vol. 31:90–97 (1966).
M. Zaoral et al., "Amino Acids and Peptides. LXXI. Synthesis of 1–Deamino–8–D–γ–Aminobutyrine–Vasopressin, 1–Deamino–8–D–Lysine–Vasopressin, and 1–Deamino–8–D–Arginine–Vasopressin," *Collection Czechoslov. Chem. Commun.*, vol. 32:1250–1257 (1967).
Collection Czechoslov. Chem. Commun., vol. 35:1716–1726 (1970).
M. Zaoral et al., "[1–β–Mercaptopropionic Acid, 8–D–Norarginine]–Vasopressin. A Further Analog with High and Specific Antidiuretic Effect," *Collection Czechoslov. Chem. Commun.*, vol. 37:3350–3351 (1972).
M. Zaoral et al., "Preparation of [1–β–Mercaptopropionic Acid, 8–D–Homoarginine]–Vasopressin," *Collection Czechoslov. Chem. Commun.*, vol. 40:905–912 (1975).
M. Zaoral et al., "[1–β–Mercaptopropionic Acid, 8–α–γ–Diaminobutyric Acid]–Vasopressin and [1β–Mercaptopropionic Acid, 8–D–Ornithine]Vasopressin. Synthesis and Biological Effects," *Collection Czechoslov. Chem. Commun., vol. 41:2088–2095 (1976).*
R. L. Huguenin et al., "Synthèse de l'Orn$^8$–vasopressine et de 1–Orn$^8$–oxytocine," vol. XLVI, Fasciculus v, No. 178–179:1669–1676 (1963).
G. Lindeberg et al., "Synthesis and Properties of 1–Deamino–8–L–homolysine–vasopressin," *Journal of Medicinal Chemistry*, vol. 15, No. 6:629–631 (1972).
G. Lindeberg et al., "Synthesis and Some Pharmacological Properties of 8–L–Homoarginine–vasopressin and of 1–Deamino–8–L–homoarginine–vasopressin," *Journal of Medicinal Chemistry*, vol. 17, No. 17:781–783 (1974).
G. Lindeberg et al., "Solid Phase Synthesis and Some Pharmacological Properties of 8–D–Homolysine–Vasopressin and 1–Deamino–8–D–Homolysine–Vasopressin," *Int. J. Peptide Protein Res.*, vol. 7:395–401 (1975).
G. Lindebereg et al., "Solid Phase Synthesis and Some Pharmacological Properties of 8–D–Homoarginine–Vasopressin and 1–Deamino–8–D–Homoarginine–Vasopressin," *Int. J. Peptide Protein Res.*, vol. 8:193–198 (1976).
M. Bodanszky et al., "Synthesis and Hormonal Activities of 8–L–Homolysine–vasopressin," *Journal of Medicinal Chemistry*, vol. 14, No. 12:1197–1199 (1971).
A. Dimeli et al., "Tryptic Splitting of Vasopressin Analogues Containing Homologues of Lysine or Arginine in Position 8," *Collection Czechoslov. Chem. Commun.*, vol. 44:2451–2454 (1979).
J. Škopková et al., "Prolonged Antidiuretic Action of Vasopressin Analogues in Relation to Their Primary Structure," *Collection Czechoslovak Chem. Commun.*, vol. 46:1850–1855 (1981).

*Primary Examiner*—Jill Warden
*Assistant Examiner*—S. G. Marshall
*Attorney, Agent, or Firm*—Leydig, Voit & Mayer, Ltd.

[57] ABSTRACT

Analogues of 8-D-homoarginine vasopressin were prepared with the general formula

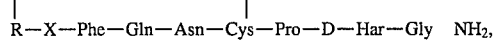

where X is L-O-methyltyrosine, L-p-ethylphenylalanine, D-p-ethylphenylalanine, L-p-methylphenylalanine or D-methylphenylalanine and R is cysteine or β-mercaptopropionic acid. These vasopressin analogues exhibited an increased affinity to uterus receptors for oxytocin, where they acted as ocytocin antagonists. Moreover, the analogues of deamino vasopressin have a significantly reduced antidiuretic activity in comparison with [8-D-arginine]vasopressin.

3 Claims, No Drawings

ANALOGUES OF 8-D-HOMOARGININE VASOPRESSIN

This is a continuation of Ser. No. 07/873,967 filed Apr. 24, 1992, now abandoned, which is a continuation-in-part of Ser. No. 07/564,538, filed Aug. 7, 1990, now abandoned.

BACKGROUND OF THE INVENTION

The present invention concerns 8-D-homoarginine vasopressin analogues.

In many laboratories great attention has been paid to the preparation of derivatives of arginine vasopressin wherein the arginine at the 8-position is replaced with D-homoarginine and the tyrosine at the 2-position is replaced with non-natural amino acids (Zaoral et al.: Collection of Czech. Chem. Commun., 31, 310, 1966; 31, 90, 1966; 32, 1250, 1967; 35, 1716, 1970; 37, 3350, 1972; 40, 905, 1975; 41, 2088, 1976; Huguenin and Boissonnas: Helv. Chim. Acta, 46, 1669, 1963; Lindeberg et al: J. Med. Chem., 15, 629, 1972; 17, 781, 1974; Lindeberg: Int. J. Peptide Prot. Res., 7, 395, 1975; Lindeberg et al.: Int. J. Peptide Prot. Res., 8, 193, 1976; Bodanszky and Lindeberg: J. Med. Chem., 14, 1197, 1971). The published results reflect modifications of some biological effects (e.g. pressoric and antidiuretic) depending on the replacement of the L-amino acid with the D-form, as well as on the shift in the position of the positively charged functional group and on the nature of the amino acid group at the 8-position of the peptide chain. This shift in the L-form of the substituent influences the accessibility of the peptide bond formed by the basic amino acid carboxyl group to trypsin cleavage (Dimeli and Barth: Collection of Czech. Chem. Commun., 44, 2451, 1979).

Increasing the distance of the guanidine group in the vasopressin (homoarginine) line retains the antidiuretic activity at almost an unchanged level (Lindeberg et al.: J. Med. Chem., 17, 781, 1974). In deamino analogues one encounters a relative decrease in antidiuretic activity (Lindeberg et al.: J. Med. Chem., 17, 781, 1974; Škopkova et al.: Collection of Czech. Chem. Commun., 46, 1850, 1981).

The replacement of L-homoarginine with its D-form in deamino analogues (Zaoral and Brtnik: Collection of Czech. Chem. Commun., 40, 905, 1975) enhances the decrease in the antidiuretic effect by more than one order of magnitude (Škopková et al.: Collection of Czech. Chem. Commun., 46, 1850, 1981).

The combined replacement of amino acid residues at both the 2- and 8-positions of the 8-L-arginine vasopressin peptide chain represents one of the most potent approaches to qualitative, as well as quantitative, alterations in the biological properties of this type of peptide (K. Jošt et al.: Handbook of Neurohypophysial Hormone Analogues, CRC Press, Boca Raton, U.S.A., 1987). A possibility for further alterations is offered by the free amino group of cysteine at the 1-position of the peptide, especially from the standpoint of prolonged action.

SUMMARY OF THE INVENTION

To obtain specifically more effective inhibitors of the neurohypophysial hormones, the analogues of vasopressin and deaminovasopressin were synthesized with D-homoarginine at the 8-position, which have been further modified by substitutions at the 2-position.

The present invention covers new analogues of 8-D-homoarginine (Har) vasopressin of the general formula:

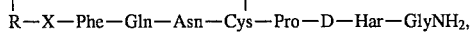

R—X—Phe—Gln—Asn—Cys—Pro—D—Har—GlyNH$_2$, where X is

L-O-methyltyrosine (compound of the formula I, VI)

L-p-ethylphenylalanine (compound of the formula II, VII)

D-p-ethylphenylalanine (compound of the formula III, VIII)

L-p-methylphenylalanine (compound of the formula IV, IX)

D-p-methylphenylalanine (compound of the formula V, X)

and R is cysteine or β-mercaptopropionic acid (Mpr).

The present invention also covers a method for the preparation of the aforementioned compounds which is based on the solid-phase, step-wise synthesis of the linear chain from hydroxybenzotriazole esters of the amino acids, appropriately protected as with tertiary-butyloxycarbonyl groups, followed by release from the resin with the simultaneous cleavage of the side-chain protecting groups, as by means of liquid hydrogen fluoride, and finally, by closing the ring, accomplished as by the action of potassium ferricyanide and separation of the peptides with L- and D-isomers of amino acids at the 2-position of the peptide chain by means of high-pressure liquid chromatography (HPLC).

The mentioned types of compounds which are able to suppress the uterotonic effect of the neurohypophysial hormones may be potentially utilized as agents for preventing premature childbirth provoked by endogenous oxytocin or vasopressin.

The compounds VIII and X belong to the most effective inhibitors of the vasopressin series prepared up to this time, as may be ascertained by reference to data contained in the Table I.

DETAILED DESCRIPTION OF THE PREFERRED EMBODIMENTS

The present compounds have unexpectedly also been found to have specific effects on blood coagulation and fibrinolytic properties. Such properties are distinguishable from the effect of [8-D-arginine]deaminovasopressin, which acts to increase the expression of Factor VIII and tPA. In contrast thereto, some of the compounds of the present invention have dissociated FVIII and tPA activities, and none increase the expression of both FVIII and tPA. Some compounds increase either the expression of FVIII or the expression of tPA but not both concurrently. Further, some compounds inhibit the expression of FVIII, tPA, or both.

N-α-tert.-butyloxycarbonyl-NG-nitrohomoarginine was found to be a suitable D-homoarginine derivative for the synthesis of all analogues, the p-methylphenylalanine and p-ethylphenylalanine residues being introduced into the molecule in the form of a mixture of L- and D-amino acids.

The synthesis of compounds of the formulas I to X was carried out employing the solid-phase method on benzhydrylamine res in. The α-amino groups were protected with the tert.-butyloxycarbonyl group (Boc), side-chain groups were blocked with the nitro group (D-homoarginine), 4-methylbenzyl(cysteine), benzyloxycarbonyl(tyrosine) and benzyl(β-mercaptopropionic acid). Condensation of the protected amino acids was carried out in dimethylformamide (DMF) using the corresponding active hydroxybenzotriazole esters. The protective groups were cleaved from the side chains with liquid hydrogen fluoride (HF), simultaneously releasing the peptide chain from the carrier. Oxidation of SH-groups and the subsequent closing of the ring were accomplished by the action of potassium ferricyanide solution. The compounds were purified and peptides with D- and L-amino acids at the 2-position were separated by means of HPLC. For the preparation of diastereo-isomeric mixtures of the analogues with D, L-p-ethylphenylalanine or D, L-p-methylphenylalanine only 1.1 equivalents of tert.-butyloxycarbonyl-D, L-p-ethylphenylalanine and tert.-butyloxycarbonyl-D,L-p-methylphenylalanine were used, respectively.

The compounds obtained were characterized by thin layer chromatography (TLC on silica plates (Sulifol, Kavalier, Czechoslovakia)) using the following solvent systems: 2-butanol-98% formic acid-water (10:3:8) or 1-butanol-acetic acid-pyridine-water (15:3:10:6). Electrophoresis on Whatmann 3 MM paper in 1M-acetic acid or in a pyridine-acetate buffer (pH 5.7), for 1 h at 20 V/cm was also employed for the characterization. Amino acid analysis was carried out on analyzers T339 or D-500 (Durrum Corp., U.S.A.). Analytical HPLC was run on the column with Sepharon IX C-18 or Vydac Z18 TP 5 and the preparative HPLC was carried out on a modular system (Knauer) on a column with Sepharon SGX-C-18.

The procedure for joining the protected amino acid to the peptide chain being formed on the carrier can be described as follows:

1. Cleavage of the Boc-group with 409 ml of 50% trifluoroacetic acid (TFA) in dichloromethane containing 2% anisole, lasting 2 min., repeated again after 30 min.
2. Rinsing with dicholoromethane (3×40 ml, duration of each rinsing 30 sec).
3. Rinsing with 30% dioxane in dichloromethane (3×40 ml, each rinsing 30 sec).
4. Rinsing with dichloromethane (as in step 2).
5. Neutralization with 10% triethylamine (40 ml) in dichloromethane (40 ml, 2 min. cycle).
6. Rinsing with dichloromethane (2×40 ml, 30 sec. cycle).
7. Neutralization with 40 ml of 10% triethylamine in 40 ml dichloromethane (2 min. cycle).
8. Rinsing with dichloromethane (6×40 ml, 30 sec cycle).
9. Addition of the hydroxybenzotriazole ester of the Boc-protected amino acid in dichloromethane, until negative ninhydrin test is achieved (30–120 min).
10. Rinsing with 50% ethanol in dichloromethane (3×40 ml, 30 sec cycle).
11. Rinsing with dichloromethane (3×15 ml, 1 min cycle).

Benzhydrylamine resin (4.46 g, 0.56 mmol/g) was suspended in dichloromethane and after rinsing with 5% triethylamine in dichloromethane and dimethylformamide, mixed with 3 molar excess of Boc-Gly-OBt. The reaction was interrupted after 30 min and the resin was rinsed subsequently with dimethylformamide (3×20 ml) and dichloromethane (3×20 ml). Then, the procedure described in Example 4 was applied. Boc-amino acids in the form of active esters (in 3 molar excess) were coupled to the amino groups of the bound amino acid in the following sequence: Boc-D-Har(NO$_2$)-OH, Boc-Pro-OH, Boc-Cys(4-Me-Bzl)-OH, Boc-Asn-OH, Boc-Gln-OH, and Boc-Phe-OH, where Bzl=benzyl. A catalyst (4-dimethylaminopyridine, 50 mg) was added to accelerate the coupling of homoarginine, cysteine and phenylalanine.

The biological activity of the peptides was tested on rats, namely: the uterotonic activity (agonistic and antagonistic) according to the Holton's method (Holtdon, J.: Brit. J. Pharmacol., 3,328, 1960) modified by Munsick (Endocrinology, 66, 451, 1960), the inhibitory activity being expressed as pA$_2$ (Eggen et al.: J. Gen. Physiol., 56, 250, 1970), the pressoric activity was determined on despinalized male rats according to Krejčí et al. (Brit. J. Pharm. Chemother., 30, 497, 1967) and the antidiuretic activity according to Burn (Burn et al.: Biol. Stand. Oxford Univ. Press, London, 1950) with [deaminol, D-arginine$^8$]vasopressin (dDAVP) used as the standard. A summary of the biological activities is presented in the Table I.

Further examples describing the preparation of compounds I to X are presented.

EXAMPLE 1

Preparation of [1-mercaptopropionic acid, 2-O-methyltyrosine 8-D-homoarginine]vasopressin (compound of the formula VI)

Boc-Tyr(Me)OH and Mpr(Bzl)OH were coupled to the resin with the bound heptapeptide (0.91 g, 0.33 mmol, where (Me)OH is methanol). The resin with the bound nonapeptide (1 g) was submitted to the action of liquid hydrogen fluoride (10 ml, 60 min, 0° C.) in the presence of anisole (1.5 ml). The hydrogen fluoride was then removed with nitrogen at 0° C. (in the course of 30 min). The mixture of the free nonapeptide and the resin was shaken with ether, filtered off and rinsed with ethylacetate. The free peptide was then dissolved in 20% acetic acid (100 ml) at 40° C., diluted with water and the solution was lyophilized. The lyophilized product was dissolved in water (300 ml) and the pH of the solution was adjusted to 7.0. Potassium ferricyanide (0.01 mol/l) was added to the solution until the color remained yellow. When the oxidation was terminated (after 30 min), the pH was adjusted to 4.5 with acetic acid. The solution was applied to a column with Amberlite CG-50I and, after rinsing with 0.25% acetic acid (150 ml), the product was eluted with 50% acetic acid (60 ml), lyophilized (47 mg) and purified by means of HPLC to afford 9 mg of the peptide. Amino acid analysis: Phe-0.87, Cys-0.91, Asp-1.01, Glu-0.98, Pro-0.96, Gly-1.00, Tyr(me)-0.96, Har-0.92.

EXAMPLE 2

Preparation of [1-mercaptopropionic acid, 2-p-ethyl-D,L-phenylalanine-8-D-homoarginine]vasopressin (compounds of the formulae VII and VIII)

Boc-L,D-p-ethylphenylalanine (1.1 equivalent) was coupled to the resin with the bound heptapeptide (1.35 g, 0.5 mmol) in the course of 24 h. Then, during 30 min, further 1 equivalent was added in the presence of dimethylaminopyridine. After the coupling of Mpr(Bzl)OH to the resin according to the scheme presented, the nonapeptide bound to the resin (1.4 g) was submitted to the action of liquid hydrogen fluoride (10 ml, 60 min, 0° C.) in the presence of anisole (1.5 ml). The hydrogen fluoride was removed with nitrogen at 0° C. (in the course of 30 min). The released nonapeptide, together with the resin, was mixed with ether, filtered off and rinsed with ethylacetate. The free peptide was then dissolved in 20% acetic acid (100 ml) at 40° C., diluted with water and the solution was lyophilized. The lyophilized product was dissolved in water (500 ml) and the pH of the solution was adjusted to 7.0 with ammonium hydroxide. Potassium ferricyanide (0.01 mol/l) was added, until the color of the solution remained yellow. When the oxidation was terminated (after 30 min), the pH was adjusted to 4.5 with acetic acid. The solution was applied to a column with Amberlite CG-50I and, after rinsing with 0.25% acetic acid (150 ml), the product was eluted with 50% acetic acid (60 ml). Lyophilization of the eluate afforded 41 mg of the product.

Separation of the racemate of [1-mercaptopropionic acid, 2-p-ethyl-D,l-phenylalanine- 8-D-homoarginine]vasopressin:

The preparative HPLC was carried out using a modular setup (Knauer setup comprising Knauer HPLC Programmer 50, Knauer HPLC Pump 364 and Knauer detector with variable wavelength setting) on a column filled with Sepharon SG-X-C-18 (10 um, 250×16 mm). The peptide was injected in the amount of 5 mg and eluted with a concentration gradient of methanol (MeOH)-start 50%, gradient 1% $min^{-1}$ (the retention time for the L-form: 10.05 min, for the D-form: 11.97 min). Yield of the L-derivative was 10 mg, that of the D-derivative was 8 mg.

Amino acid analysis: L-form: EtPhe-0.80, Phe-1.03, Cys-0.93, Asp-0.95, Glu-1.12, Pro-0.98, Gly-1.00, Har-0.87; D-form: tPhe-0.85, Phe-1.00, Cys-0.93, Asp-0.93, Glu-1.16, Pro-0.97, Gly-1.03, Har-0.87.

EXAMPLE 3

Preparation of [1-mercaptopropionic acid, 2-p-methyl-D,L-phenylalanine-8-D-homoarginine]-vasopressin (compounds of the formulae IX and X)

Boc-L,D-p-MePhe-OH and Mpr(Bzl)OH were coupled to the resin with the bound heptapeptide (1.35 g, 0.5 mmol) according to the procedure described in Example 7. Peptides were released from the resin and isolated as described in Example 7. Yield: 50 mg of the peptide.

Separation of the racemate [1-mercaptopropionic acid, 2-p-methyl-D,L-phenylalanine- 8-D-homcarginine]vasopressin:

Separation of the mixture was carried out as in Example 2. Under the conditions stated, the mobility of the L-p-methylphenylalanine isomer is higher (retention time 13.57–13.73 min) in comparison to that of the D-isomer (retention time 15.72–15.75 min). Yield of the L-derivative: 4.2 mg, of the D-derivative: 5.6 mg.

Amino acid analysis: L-form: MePhe-0.90, Phe-1.03, Cys-1.05, Asp-0.97, Glu-1.13, Pro-0.99, Gly-1.05, Har-0.87; D-form: MePhe-0.87, Phe-1.00, Cys-1.06, Asp-0.95, Glu-1.10, Pro-1.00, Gly-1.06, Har-0.87.

EXAMPLE 4

Preparation of [2-O-methyltyrosine, 8-D-homoarginine]vasopressin (compound of the formula I)

Boc-Tyr(Me)OH and Boc-Cys(4-Me-Bzl)OH were coupled to the resin with the bound heptapeptide (1.7 g, 0.48 mmol) according to the following general scheme.

The resin with the coupled nonapeptide (1.8 g) was submitted to the action of liquid hydrogen fluoride (20 ml, 60 min, 0° C.) in the presence of anisole (1.0 ml) and 1,2-ethandithiole (1 ml). The hydrogen fluoride was removed with nitrogen at 0° C. (in the course of 30 min). The released nonapeptide, together with the resin, was mixed with ether, filtered off and rinsed with ethylacetate. The free peptide was extracted with 50% acetic acid, acetic acid and water and finally, lyophilized (yield 0.69 g). The lyophilized product was dissolved in water (700 ml) and the pH of the solution was adjusted to 7.0 with sodium hydroxide (0.1 mol/l). Potassium ferricyanide (0.01 mol/l) was added, until the color of the solution remained yellow. The pH of the solution was maintained at 7.2 during the oxidation (20 min) by means of sodium hydroxide solution (0.1 mol/l), then it was adjusted to 4.45 with acetic acid. The solution was applied to a column with Amberlite CG-50I and, after rinsing with 0.25% acetic acid, the product was eluted with 50% acetic acid (60 ml), lyophilized (353 mg) and purified on a column Vydac TP5 by methanol elution (linear gradient 20%–40% MeOH-0.05% trifluoroacetic acid). Lyophilization yielded 160 mg of the product.

Elemental analysis: for $C_{48}H_{67}N_{13}O_{12}S_2 \times 3$ TFA×2 $H_2O$ calculated: 43.26% C, 5.18% H, 14.01% N; found: 42.92% C, 4,92% H, 14 . 31% N. Amino acid analysis: Asp-1.00, Glu-1.00, Pro-0.75, Gly-0.99, Cys-1.87, Tyr(me)-1.1, Phe-1.07, Har-1.05.

EXAMPLE 5

Preparation of [2-p-ethyl-L-phenylalanine, 8-D-homoarginine]vasopressin (compound of the formula II)

The resin with the bound heptapeptide (1.35 g, 0.5 mmol-Example 4) was subjected to reaction with 1.1 equivalent of Boc-L,D-Phe(p-Et)-OH for 24 h, with further 1 equivalent in the presence of dimethylaminopyridine for 30 min, and finally, with Boc-Cys(4-Me-Bzl)OH. After removing the Boc-protective group, the resin was mixed with hydrogen fluoride (15 ml, 60 min, 0° C.) in the presence of anisole (2 ml). The released nonapeptide was, together with the resin (after removing hydrogen fluoride with nitrogen), mixed with ether, filtered off, rinsed with ethylacetate and the free peptide was extracted subsequently with acetic acid, 50% acetic acid and water and finally, neutralized to the pH value of 7.0 with sodium hydroxide (0.1 mol/l). Potassium ferricyanide (0.01 mol/l) was added, until the color of the solution remained yellow. The pH of the solution was maintained at 7.2 during the oxidation (20 min) by means of sodium hydroxide solution (0.1 mol/l), then it was adjusted to 4.5 with acetic acid. The solution was applied to a column with Amberlite CG-50I and, after rinsing with 0.25% acetic acid, the product was eluted with 50% acetic acid, lyophilized (185 mg) and purified by means of HPLC on a column with Sepharon SGX C-18 by a linear gradient MeOH (20–70%)-0.1% TFA. The first peak was characterized by a mobility k'=2.2, MeOH-0.05% TFA (6:4) and k'=7.47, MeOH-0.05% TFA (5:5), and corresponded to the analogue with p-ethyl-L-phenylalanine at position 2.

For $C_{49}H_{71}N_{15}O_{11}S_2 \times 4$ TFA×2 $H_2O$ (1602.5) calculated: 42.79% C, 4.97% H, 13.11% N; found: 42.85% C, 5.05% H, 13.37% N. Amino acid analysis: Asp-0.99, Glu-1.00, Pro-1.12, Gly-1.01, Cys (determined as cysteic acid)-2.12, 4-Et-Phe-0.78, Phe-1.02, Har-0.80. Yield 18 mg.

EXAMPLE 6

Preparation of [2-p-ethyl-D-phenylalanine, 8-D-homoarginine]vasopressin (compound of the formula III)

The compound was prepared according to the procedure described in Example 5, in a mixture with compound II, from which it has been separated by means of HPLC on a column with Sepharon SGX C-18 as described in ]Example 4. The compound III was eluted in the second peak, after the linear gradient MeOH-0.05% TFA (20–70%) had been applied and is characterized by the following parameters: k'=3,60, MeOH-0.05% TFA (6:4), k'=19,57 MeOH-0.05 % TFA (5:5).

For $C_{49}H_{71}N_{15}O_{11}S_2 \times 4$ TFA (1566.4) calculated: 43.71% C, 4.83% H, 13.41% N; found: 43.74% C, 5.16% H, 13.52% N.

Amino acid analysis: Asp-1.00, Glu-0.98, Pro-1.05, Gly-1.12, Cys (determined as cysteic acid)-2.02, 4-Et-Phe-0.68, Phe-1.05, Har-0.85.

EXAMPLE 7

Preparation of [2-p-methyl-L-phenylalanine, 8-D-homoarginine]vasopressin (compound of the formula IV)

The resin with the bound heptapeptide (3.4 g, 0.96 mmol) was treated according to the scheme described. With 1.1 equivalent of Boc-L,D-Phe(p-Me)-OH for 18 h and with further 0.5 equivalent for 4 h. Then the amino acid Boc-Cys(4-Me-Bzl)-OH was attached. The resin with the coupled protected peptide was treated then according to the procedure described in Example 5. Elution with 50% acetic acid from the column with Amberlite CG-50I afforded 614 mg of the crude product which was lyophilized and purified further by means of HPLC on a column Vydac 218 TP5 by the elution with a linear concentration gradient MeOH (25–60%)-0.05% TFA. [2-p-methyl-L-phenylalanine, 8-D-homoarginine]vasopressin was eluted in the first peak (in the yield of 40 mg), the characteristics of which were as follows: k'=3.18, MeOH-0.05% TFA (55:45).

For $C_{48}H_{67}N_{13}O_{12}S_2 \times 3$ TFA$\times 2$ H$_2$O (1474.4) calculated: 43.99% C, 5.20% H, 14.25% N; found: 44.19% C, 4.96% H, 14.41% N.

Amino acid analysis: Asp-1.08, Glu-1.01, Pro-0.87, Gly-1.08, Cys (determined as cysteic acid)-2.04, 4-Me-Phe-0.70, Phe-0.92, Har-1.01.

EXAMPLE 8

Preparation of [2-p-methyl-D-phenylalanine, 8-D-homoarginine]vasopressin (compound of the formula V)

The compound was prepared according to the procedure described in the Example 7 in a mixture with compound IV and separated from it by HPLC on a column Vydac 218 TP5 by elution with a linear concentration gradient MeOH (25–60%)-0.05% TFA. [2-p-methyl-D-phenylalanine, 8-D-homoarginine ]vasopressin was eluted in the second peak (16.2 mg), the characteristics of which were as follows: K'=5.18, MeOH-0.05% TFA (55:45).

For $C_{48}H_{67}N_{13}O_{12}S_2 \times 3$, 5 TFA$\times 1$ H$_2$O (1522.4) calculated: 43.39% C, 5.005% H, 13.80% N; found: 43.24% C, 4.78% H, 14.13% N.

Amino acid analysis: Asp-0.89, Glu-1.02, Pro-1.00, Gly-1.05, Cys (determined as cysteic acid)-2.03, 4-Me-Phe-0.88, Phe-1.00, Har-1.08.

EXAMPLE 9

Compounds of the present invention ware evaluated for their ability to affect blood coagulation and fibrinolytic properties. The compounds were compared with [8-D-argenine]deamino vasopressin in squirrel monkeys. The results are shown in Table II. The findings of dissociated blood coagulation/fibrinolytic properties and the inhibitory properties are new and surprising properties for the series of vasopressin derived peptides.

TABLE I

Survey of Some Biological Activities in comparison with the know compounds

| Compound | Designation | Uterotonic activity | Pressoric activity | Antidiuretic activity |
|---|---|---|---|---|
| [D—Har$^8$] vasopressin | | 0.9 IU/mg | not determined | ~1% dDAVP |
| [Mpr$^1$, D—Har$^8$] vasopressin | | 0.8 IU/mg | 0.28 IU/mg | ~5% dDAVP |
| [O—Me—Tyr$^2$, D—Har$^8$] vasopressin | I | pA$_2$ = 7.7 | 0.04 IU/mg | not determined |
| [L-p-EtPhe$^2$, D—Har$^8$] vasopressin | II | pA$_2$ = 7.40 | pA$_2$ = 6.5 | <0.1% dDAVP |
| [D-p-EtPhe$^2$, D—Har$^8$] vasopressin | III | pA$_2$ = 8.15 | pA$_2$ = 6.5 | <0.1% dDAVP |
| [L-p-MePhe$^2$, D—Har$^8$] vasopressin | IV | pA$_2$ = 6.85 | 0.04 IU/mg | <0.1% dDAVP |
| [D-p-MePhe$^2$, D—Har$^8$] vasopressin | V | pA$_2$ = 6.85 | 0.04 IU/mg | <0.1% dDAVP |
| [Mpr$^1$, OMeTyr$^2$, D—Har$^8$] vasopressin | VI | pA$_2$ = 8.1 | 0 | not determined |
| [Mpr$^1$, L-p-EtPhe$^2$, D—Har$^8$] vasopressin | VII | pA$_2$ = 8.0 | pA$_2$ = 6.2 | <1% dDAVP |
| [Mpr$^1$, D-p-EtPhe$^2$, D—Har$^8$] vasopressin | VIII | pA$_2$ = 8.63 | pA$_2$ = 6.35 | <1% dDAVP |
| [Mpr$^1$, L-p-MePhe$^2$, D—Har$^8$] vasopressin | IX | pA$_2$ = 8.38 | pA$_2$ = 6.2 | <1% dDAVP |
| [Mpr$^1$, D-p-MePhe$^2$, D—Har$^8$] vasopressin | X | pA$_2$ = 8.68 | 0 | <1% dDAVP |

TABLE II

FVIII and tPA activity of analogues of [8-D-homoarginine] diamino vasopressin in squirrel monkeys

| Compound | FVIII/% | tPA/% |
|---|---|---|
| Control (saline) | 100% (basal value) | 100% (basal value) |
| [8-D-arginine] deamino vasopressin | 149 | 138.9 |
| [8-D-homoarginine] deamino vasopressin | 127 | 88 |
| [2-L-p-Methylphenylalanine, 8-D-homoarginine] deamino vasopressin | 155 | 67 |
| [2-D-p-Methylphenylalanine, 8-D-homoarginine] deamino vasopressin | 112 | 81 |
| [2-L-p-Ethylphenyl alanine, 8-D-homoarginine] deamino vasopressin | 111.5 | 79.4 |
| [2-L—O-Methyltyrosine, 8-D-homoarginine] deamino vasopressin | 98.5 | 116.5 |
| [2-L-p-Methylphenylalanine, 8-D-homoarginine] vasopressin | 85 | 77 |
| [2-D-p-Methylphenylalanine, 8-D-homoarginine] vasopressin | 55 | 65 |

We claim:
1. Analogues of 8-D-homoarginine vasopressin of the general formula

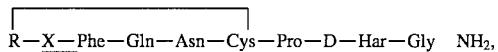

R—X—Phe—Gln—Asn—Cys—Pro—D—Har—Gly NH$_2$, where X is
  L-O-methyltyrosine
  L-p-ethylphenylalanine
  D-p-ethylphenylalanine
  L-p-methylphenylalanine
  D-p-methylphenylalanine
and R is cysteine or β-mercaptopropionic acid.

2. An analogue of claim 1 wherein X is D-p-ethylphenylalanine and R is β-mercaptopropionic acid.

3. An analogue of claim 1 wherein X is D-p-methylphenylalanine and R is β-mercaptopropionic acid.

* * * * *